(12) United States Patent
Gilson et al.

(10) Patent No.: US 10,434,328 B2
(45) Date of Patent: Oct. 8, 2019

(54) NON-INVASIVE IN VIVO DEEP NERVE CELL STIMULATION SYSTEM AND METHOD

(71) Applicants: Richard D. Gilson, Oviedo, FL (US); Nizam Razack, Orlando, FL (US)

(72) Inventors: Richard D. Gilson, Oviedo, FL (US); Nizam Razack, Orlando, FL (US)

( * ) Notice: Subject to any disclaimer, the term of this patent is extended or adjusted under 35 U.S.C. 154(b) by 544 days.

(21) Appl. No.: 14/943,474

(22) Filed: Nov. 17, 2015

(65) Prior Publication Data

US 2016/0144196 A1  May 26, 2016

Related U.S. Application Data

(60) Provisional application No. 62/080,632, filed on Nov. 17, 2014.

(51) Int. Cl.
*A61N 5/06* (2006.01)
*A61N 7/02* (2006.01)
(Continued)

(52) U.S. Cl.
CPC ............ *A61N 5/0622* (2013.01); *A61B 34/30* (2016.02); *A61N 7/02* (2013.01); *A61B 2090/374* (2016.02); *A61N 2005/067* (2013.01); *A61N 2005/0647* (2013.01); *A61N 2005/0659* (2013.01); *A61N 2005/0661* (2013.01); *A61N 2005/0662* (2013.01); *A61N 2007/0021* (2013.01)

(58) Field of Classification Search
CPC .............................. A61N 7/00; A61H 23/0245
See application file for complete search history.

(56) References Cited

U.S. PATENT DOCUMENTS 8,024,049 B1  9/2011  Gilson et al.
8,032,231 B1  10/2011  Gilson et al.
(Continued)

OTHER PUBLICATIONS

Shapiro et al., "Infrared light excites cells by changing their electrical capacitance", Nature Comm., 2012, 3:376, 10 pages.
(Continued)

*Primary Examiner* — Hien N Nguyen
(74) *Attorney, Agent, or Firm* — Brian S. Steinberger; Hilary F. Steinberger; Law Offices of Brian S. Steinberger, P.A.

(57) ABSTRACT

In one embodiment, a system for stimulating neurons of a patient in vivo is provided herein. The system includes a first energy emitting component positioned external to the patient configured to generate a first energy stimulus, and a second energy emitting component positioned external to the patient configured to generate a second energy stimulus, wherein the first energy stimulus comprises an intensity level below a predetermined threshold required to stimulate the neurons, and wherein the second energy stimulus comprises an intensity level below a predetermined threshold required to stimulate the neurons; wherein a combination of the first and second energy stimuli at a target location in a target tissue of a patient comprises an intensity level at or above a predetermined threshold required to stimulate the neurons in the target tissue and prevent the stimulation of neurons outside the target location.

8 Claims, 12 Drawing Sheets

(51) Int. Cl.
 *A61B 34/30* (2016.01)
 *A61N 5/067* (2006.01)
 *A61N 7/00* (2006.01)
 *A61B 90/00* (2016.01)

(56) References Cited

U.S. PATENT DOCUMENTS

| | | |
|---|---|---|
| 8,849,408 B1 | 9/2014 | Gilson et al. |
| 9,278,208 B1 | 3/2016 | Gilson et al. |
| 2003/0050527 A1* | 3/2003 | Fox .................... A61N 2/02 600/13 |
| 2009/0209852 A1* | 8/2009 | Mate .................. A61B 90/16 600/431 |
| 2010/0007512 A1* | 1/2010 | Ghovanloo ............ G06F 3/011 340/4.11 |
| 2010/0113959 A1* | 5/2010 | Pascual-Leone ...... A61N 2/006 600/544 |
| 2011/0125212 A1* | 5/2011 | Tyler ................. A61N 1/0551 607/42 |
| 2011/0178441 A1* | 7/2011 | Tyler .................. A61N 7/00 601/2 |
| 2014/0074176 A1 | 3/2014 | Jansen et al. |
| 2014/0187875 A1* | 7/2014 | Paris ................... A61B 5/6803 600/301 |
| 2014/0275716 A1* | 9/2014 | Connor .............. A61N 1/36057 600/9 |
| 2015/0170504 A1* | 6/2015 | Jooste ................ A61B 5/6898 340/539.12 |
| 2015/0339444 A1* | 11/2015 | Kimmel ................ H04L 67/32 709/219 |
| 2015/0360026 A1* | 12/2015 | Wagner .............. A61N 1/36025 601/2 |

OTHER PUBLICATIONS

Duke et al., "Transient and Selective Suppression of Neural Activity with Infrared Light", Nature Comm., Scientific Reports 3, Sep. 2013, Article No. 2600, DOI: 10.1038, 8 pages.

Sohal et al., "Insights into Cortical Oscillations Arising from Optogenetic Studies", Biol Psychiatry, 2012, 71(12): 1039-1045. doi:10.1016/j.biopsych.2012.01.024.

* cited by examiner

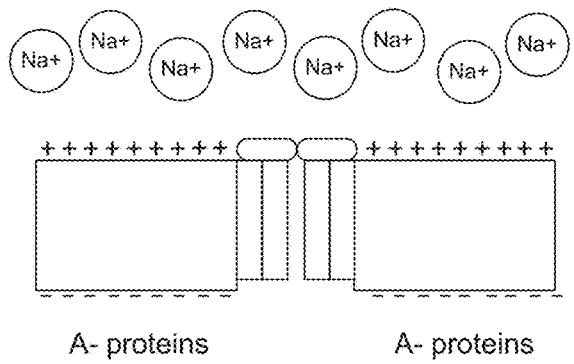
FIG. 4A
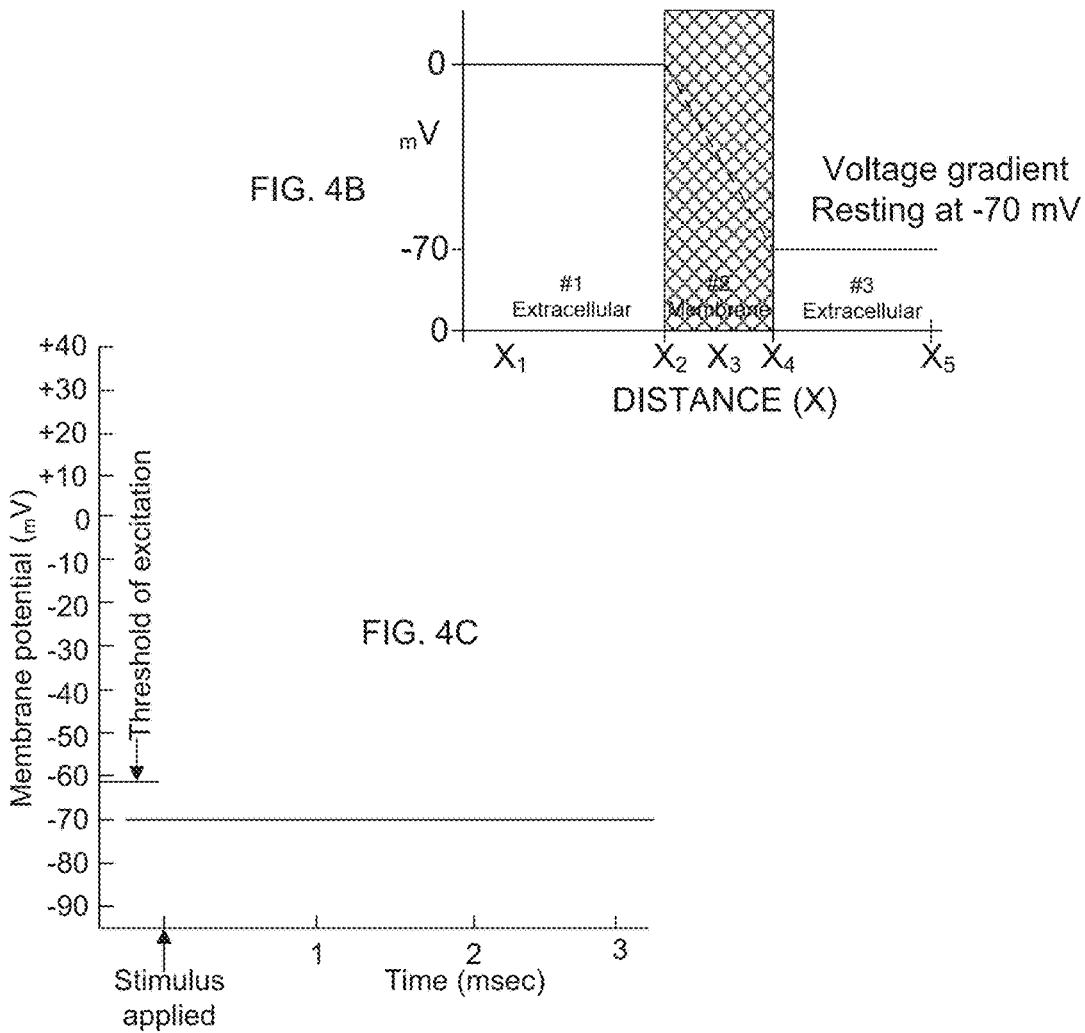
FIG. 4B
FIG. 4C

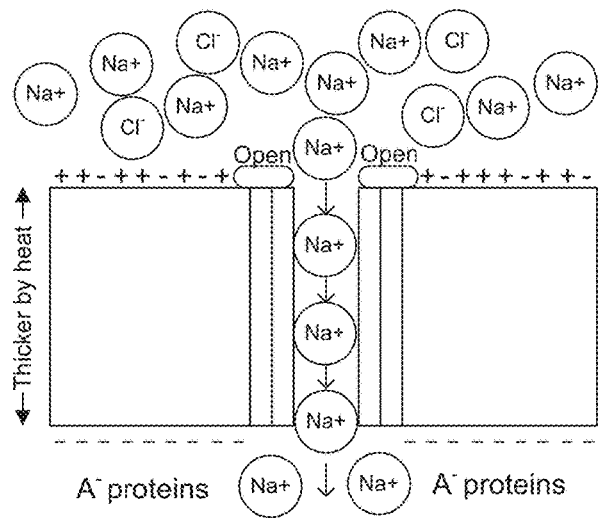
FIG. 5A
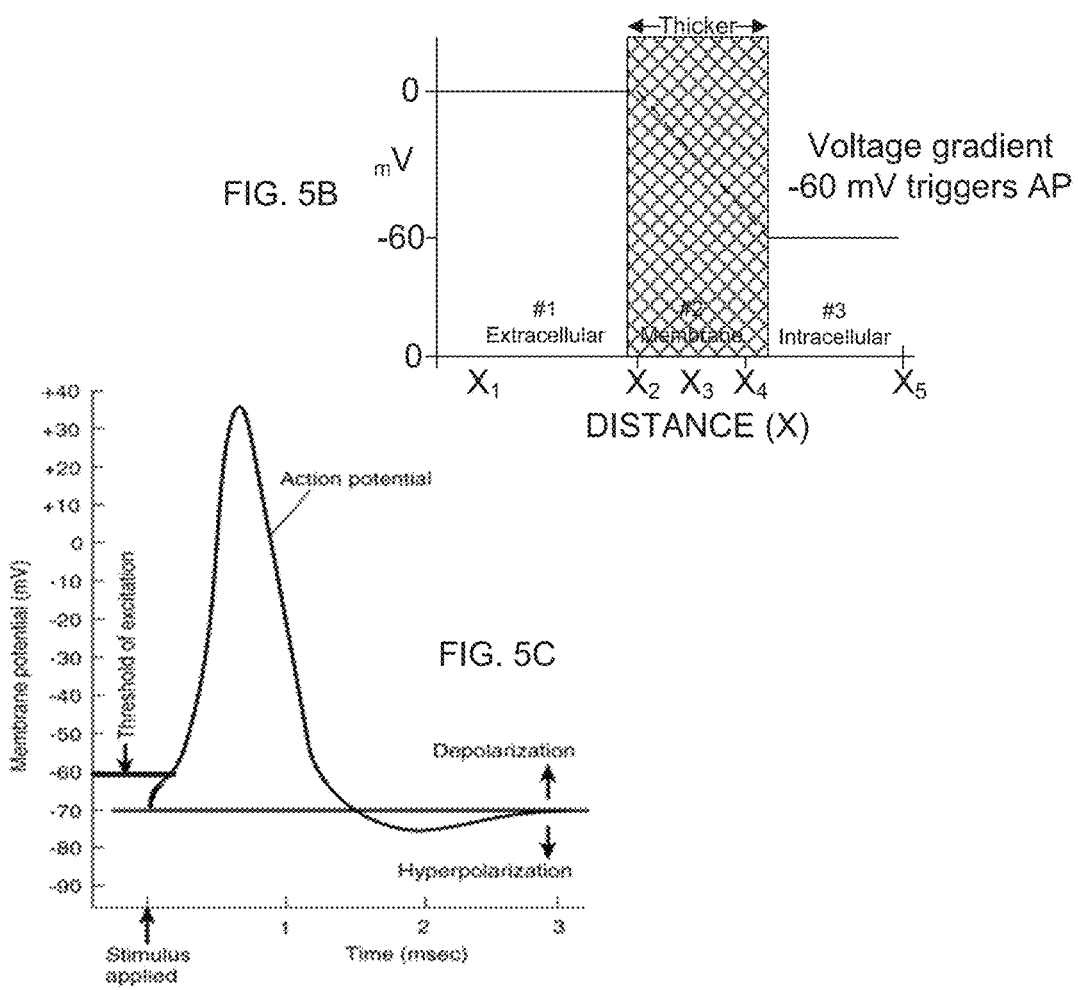
FIG. 5B
FIG. 5C

NON-INVASIVE IN VIVO DEEP NERVE CELL STIMULATION SYSTEM AND METHOD

BACKGROUND

Deep brain stimulation (DBS) with electric current is a useful method in treating a wide variety of disorders including Parkinson's disease, narcolepsy, OCD, chronic pain, major depression and even obesity. In DBS, electrodes are implanted in specific areas of the brain and nearby neurons are stimulated with patterns of current generated by a neuro stimulator connected with wires to the electrodes.

Neurons include dendrites which are a branched pattern of processes which act to receive information and extend from a cell body (soma) which integrates the information received by the neuron and provides for the metabolic needs of the neuron, and an axon extending from the soma which transports constituents between the soma and distant synapses, wherein the synapses transfer information to the next set of nerve dendrites.

Neurons are negatively polarized in their resting state. Therefore, when no stimulation is presented, inside the soma membrane of the neuron, there exists a negative charge relative to the outside of the membrane. Sending a stimulation signal to the inner brain requires an action potential created by depolarization of the soma membrane which travels by way of axons to the inner brain, for example. Therefore, information moves through the nervous system as a series of action potentials that travel between the neurons by way of axon membranes.

A number of neurological disorders and many neurodegenerative diseases like Parkinson's disease involve, or eventually progress to involvement of both brain hemispheres; requiring electrode implants in both sides. Electrode implants may require an invasive procedure to implant the electrodes into the cranial cavity in a position in which portions of the brain can be stimulated during use. In some instances these electrodes may be incorrectly positioned. In other instances, there may be an electrode shift post-implantation. In both cases, subsequent surgical procedures would be required to adjust the positions of the electrodes and/or re-implant them. These additional brain surgeries result in unnecessary risks to a patient that can and should be avoided.

SUMMARY

In one embodiment, a system for stimulating neurons of a patient in vivo is provided herein. The system includes a first energy emitting component positioned external to the patient configured to generate a first energy stimulus, and a second energy emitting component positioned external to the patient configured to generate a second energy stimulus, wherein the first energy stimulus comprises an intensity level below a predetermined threshold required to stimulate the neurons, and wherein the second energy stimulus comprises an intensity level below a predetermined threshold required to stimulate the neurons; wherein a combination of the first and second energy stimuli at a target location in a target tissue of a patient comprises an intensity level at or above a predetermined threshold required to stimulate the neurons at the target location in the target tissue and prevent the stimulation of neurons outside the target location.

In another embodiment, a method of stimulating neurons in vivo is provided herein. The method includes generating a first energy stimulus and a second energy stimulus, directing the first and second energy stimuli at a target location in a tissue of a patient having neurons to be stimulated, wherein the intensity of the first energy stimulus and the second energy stimulus are each below a predetermined threshold level required to independently stimulate one or more neurons in the target tissue, and wherein the combination of the first and second energy stimuli at the target location comprise an intensity at or above the predetermined threshold level to stimulate the one or more neurons at the target location and prevent the stimulation of neurons outside the target location.

BRIEF DESCRIPTION OF THE DRAWINGS

FIGS. 4A-C are schematic and graphical illustrations showing an example of a voltage gradient of a resting neural cell with a closed pore preventing movement of ions across the membrane showing the resting state of the neural cell.

FIGS. 5A-C are schematic and graphical illustrations showing the effect of heat on the neural membrane causing the pore to open allowing the movement of ions across the membrane, lowering the voltage gradient of the membrane and increasing the action potential of the neuron caused by neural stimulation in one embodiment.

DETAILED DESCRIPTION

Figure 1:
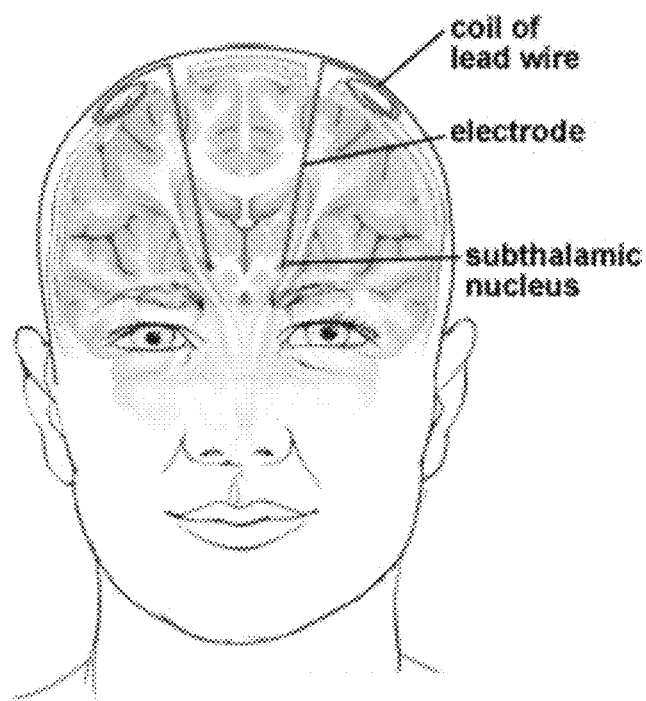
FIG. 1 is a view of a prior art method of deep brain stimulation with surgically implanted electrodes.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

Definitions:

The term "energy" as used herein includes light or visible energy, electromagnetic radiation, ultrasound energy, electromotive radiation, among other types of energy known to those skilled in the art. The term light is inclusive of visible light as well as ultraviolet and infrared light, and is not intended to be limiting. Electromagnetic radiation includes infrared laser light and any other type of electromagnetic radiation known in the art, including visible light and ultraviolet light.

As used herein, the terms "subject", "user" and "patient" are used interchangeably. As used herein, the term "subject" refers to an animal, preferably a mammal such as a non-primate (e.g., cows, pigs, horses, cats, dogs, rats etc.) and a primate (e.g., monkey and human).

As used herein, the terms a "first energy emitting component" and a "second energy emitting component", and a "first energy stimulus" and a "second energy stimulus" are not intended to be limiting. Greater or fewer energy emitting components and energy stimuli may be used herein. The stimuli described herein include but are not limited to pulsed or continuously delivered stimuli. More than one stimulus may be provided from an energy emitting component, in non-limiting examples, and as described herein, stimuli may be provided from multiple energy emitting components. Any number of energy emitting components may be provided herein.

Embodiments disclosed herein provide a non-invasive system and method that precisely delivers stimulus energy to targeted nerve cells in vivo, in a non-limiting example, to neural tissue in specified areas of the brain. An exoskeleton frame (or frames) may hold the device allowing accurate focus of multiple external stimuli of penetrating energy to mutually collide at one or multiple sites within the brain or other body areas. Many different types of stimulus energies may be used, including but not limited to optical, ultrasound, electromagnetic, or low-level radiation energy, for example, to trigger nerve cells. These nerve cells are basically unstable electrical units.

In non-limiting embodiments, the stimuli can be energized for deep penetration through living tissue. When aimed at target tissue with precision, a focal point at which the stimuli or beams of stimulus energy intersect can be located at the target tissue to be energized. These stimuli of energy can be directed to collide at a confined focal point or points at the target tissue region or regions, for example, at targeted neural cells. Some types of stimulus energies may disperse diffusively, but the sizes, shapes, and distributions of their components can be manipulated to generate an increased irradiance over a specific area or at a specific point as provided in the embodiments herein. Embodiments of the invention, in a non-limiting example, can be used to target areas within the hypothalamus region which can be used to trigger behavioral changes which may be immediately realized.

In a further non-limiting embodiment, the specificity of targeted cells, in particular, can be further increased by genetically modifying only those neurons of interest to express opsin protein such that they become highly sensitive to light. One technique that may be employed to achieve this result is that of optogenetics. Optogenetics includes the modification of neural genes to express channelrhodopsin2, which is a protein that forms ion channels that open in response to light, allowing the neurons to become more sensitive to light stimulation. Using this technique to create neurons which are particularly sensitive to light provides the ability to direct a light energy beam that is of a lesser intensity toward the target tissue than what would otherwise be required to excite the target tissue, further decreasing risk of damage to tissue surrounding the target area through which the light energy beam may be passed.

The target point or points as discussed herein have an additive effect of the summed energies of the colliding stimuli directed thereto, allowing weaker diffuse radiation to spread elsewhere inertly. The intensity of individual stimulus energies may therefore be adjusted below the threshold level of stimulation through their entry paths of neural tissue and beyond because of diffusion, preventing activation of untargeted neurons. The energy stimuli may be continuously directed at the target tissue region, or may be applied in adjustable increments of time, for example. Therefore, behavioral modifications may be triggered continuously or sequentially in adjustable pulses or waves (by phase, amplitude, pulse width and frequency, in non-limiting examples) to achieve maximal research and therapeutic efficacy. Such precise non-invasive stimulation is extremely useful for exploratory work, highly-controlled research, and therapeutic purposes.

Emitted energy stimuli such as light (photo) emissions, ultrasound emissions, or other controlled heat emitting components can provide a deep-tissue penetrating 'universal stimulus' that can activate any nerve cell—CNS, PNS, sensory, motor, etc. This may occur by triggering the axon of the nerve cell at the focal-targeted locations. Typically, nerve cell dendrites and soma act to block most spurious stimuli from activating a neuron through the axon hillock portion of the nerve cell, thereby providing stimulus protection by selectively filtering out all but stimuli specific to the cell, i.e., neuro-chemicals, environmental energies, etc. However, it has been discovered herein that by using focused heating and/or cooling as a 'universal stimulus' to excite the axon, reversible neuron firing can be achieved.

Figure 6A:
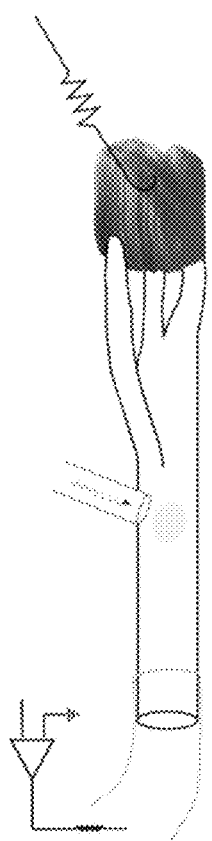
FIGS. 6A-C include graphical and schematic illustrations of the transient and selective inhibition of neural activity with infrared light and electrical stimulation.
Figure 6C:
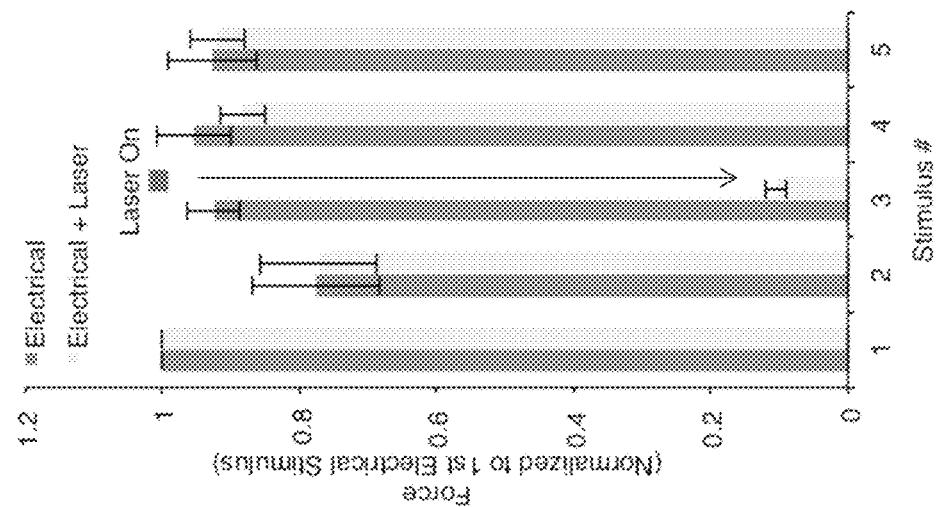
Figure 6B:
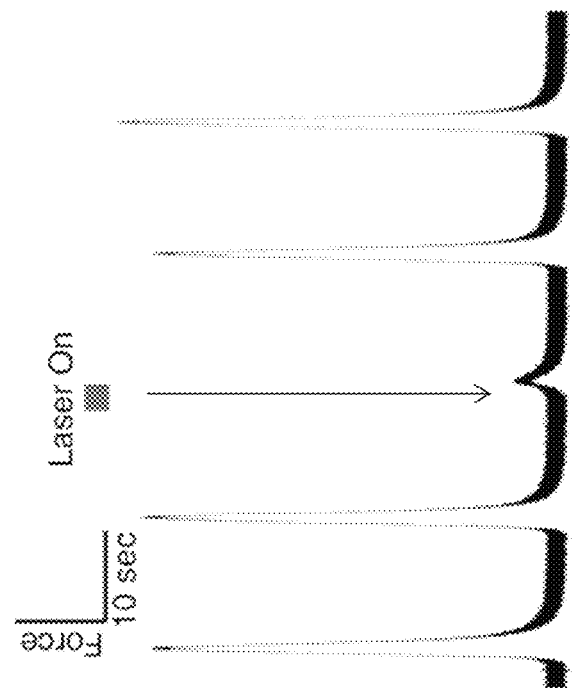
Figure 7A:
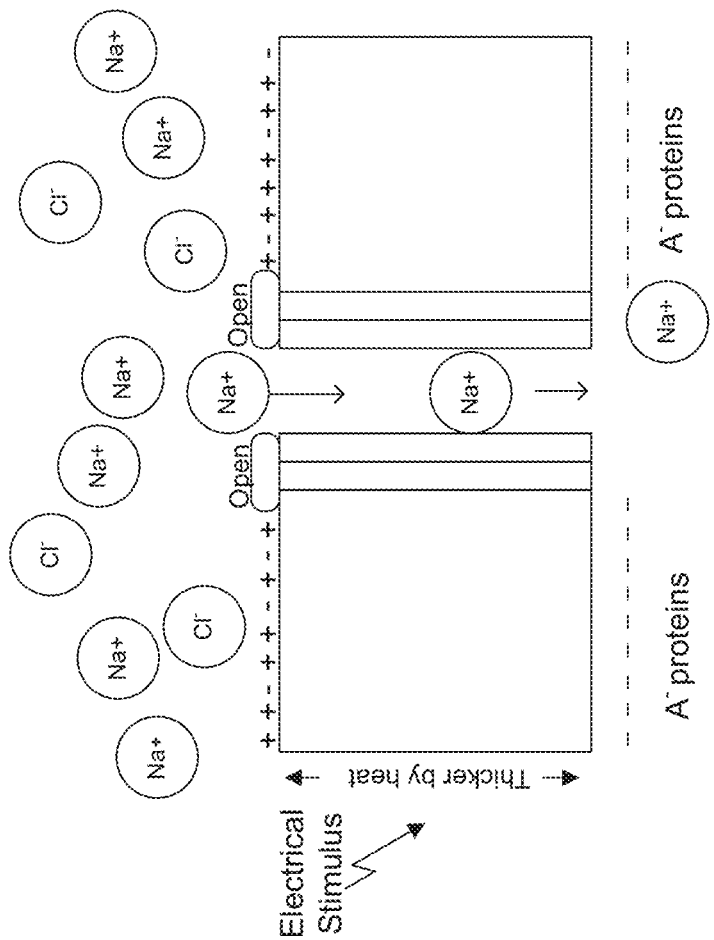
FIGS. 7A-B include schematic and graphical illustrations of the effect of heating (stimulating) during firing of a neuron resulting in a decrease in the voltage gradient, a depletion of available ions and influx and suppression of the action potential of the neuron.
Figure 7B:
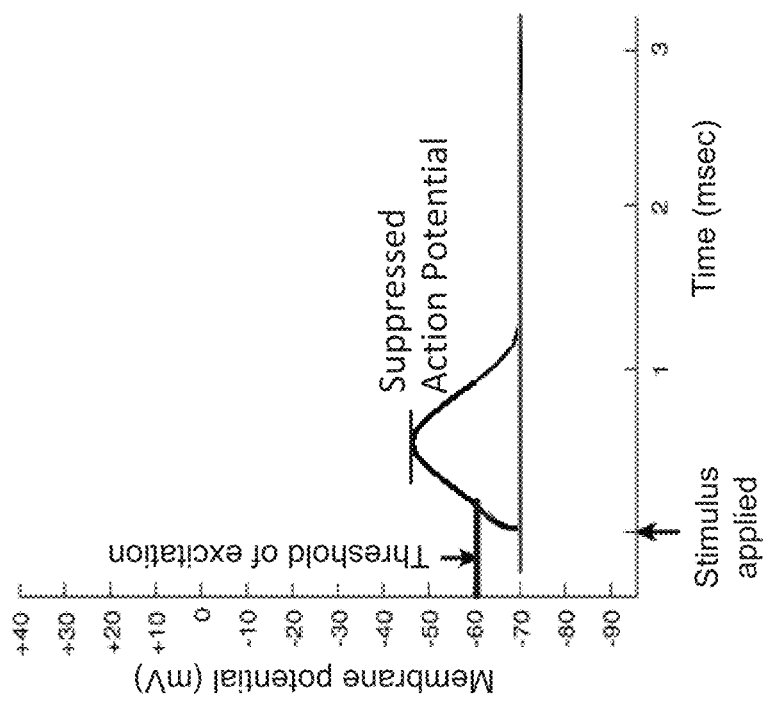

Ultrasound and electromotive radiation (EMR), for example, act as concentrated thermal components to heat, rapidly and significantly, expanding the axonal membrane. This thickening brings about firing by thermal expansion of the double lipoid membrane layer. The thicker double lipoid layer and greater distances between its surfaces provides less force attracting opposing ions close to the lipoid surfaces which creates less voltage across the membrane. Therefore, with less attracting force, the ion surface concentration dilutes, e.g., on the outside, $Na^+$ ions mix with more $Cl^-$ ions lowering overall voltage and lessening the membrane polarization. When the neuronal membrane depolarizes to its threshold, it triggers voltage-sensitive active channels along the axon, for example, (among other potential locations including the soma and dendrites) opening these channels, and allowing Na$^+$ ions to rush in, initiating the action potential that propagates down to the axonal ending. The action potential is stopped upstream by the axon hillock, preventing back-propagation of the signal. In a non-limiting example, infrared pulses are absorbed by water, producing a rapid local increase in temperature. This heating reversibly alters the electrical capacitance of the plasma membrane, depolarizing a target cell. In another embodiment, a combination of electrical stimulation with infrared laser pulses inhibits activity of neurons as shown in Duke et al., U.S. Patent Publication 20140074176. FIGS. 6A-C include graphical and schematic illustrations from Duke et al., showing the transient and selective inhibition of neural activity with infrared light and electrical stimulation and pertain to information disclosed in Duke et al. The transient and selective inhibitive effects of neural activity with infrared light and electrical stimulation are also shown in FIGS. 7A-B, described in more detail below.

In another embodiment, it has been identified herein that infrared light can be used to selectively inhibit neural activity. A combination of electrical stimulation and infrared light can selectively and transiently inhibit neural activity when directed at a target tissue by decreasing the voltage gradient across the neural membrane, depleting available ions and influx, and suppressing action potential of the neurons.

Figure 8A:
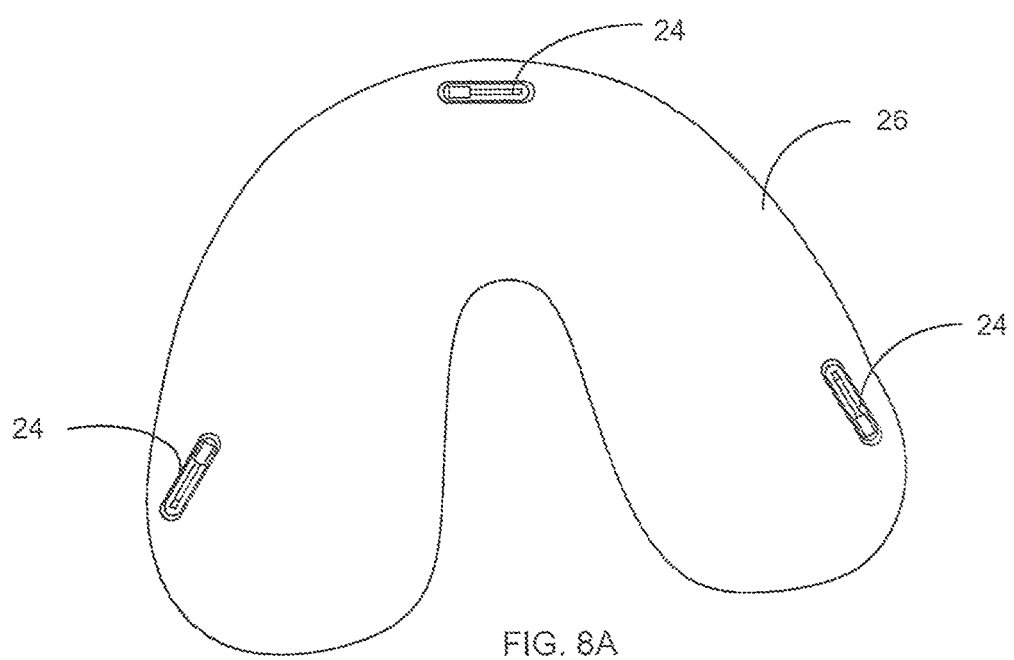
FIGS. 8A-B include a plan view and a bottom elevation view of embodiments of retaining devices comprising transponder components.
Figure 8B:
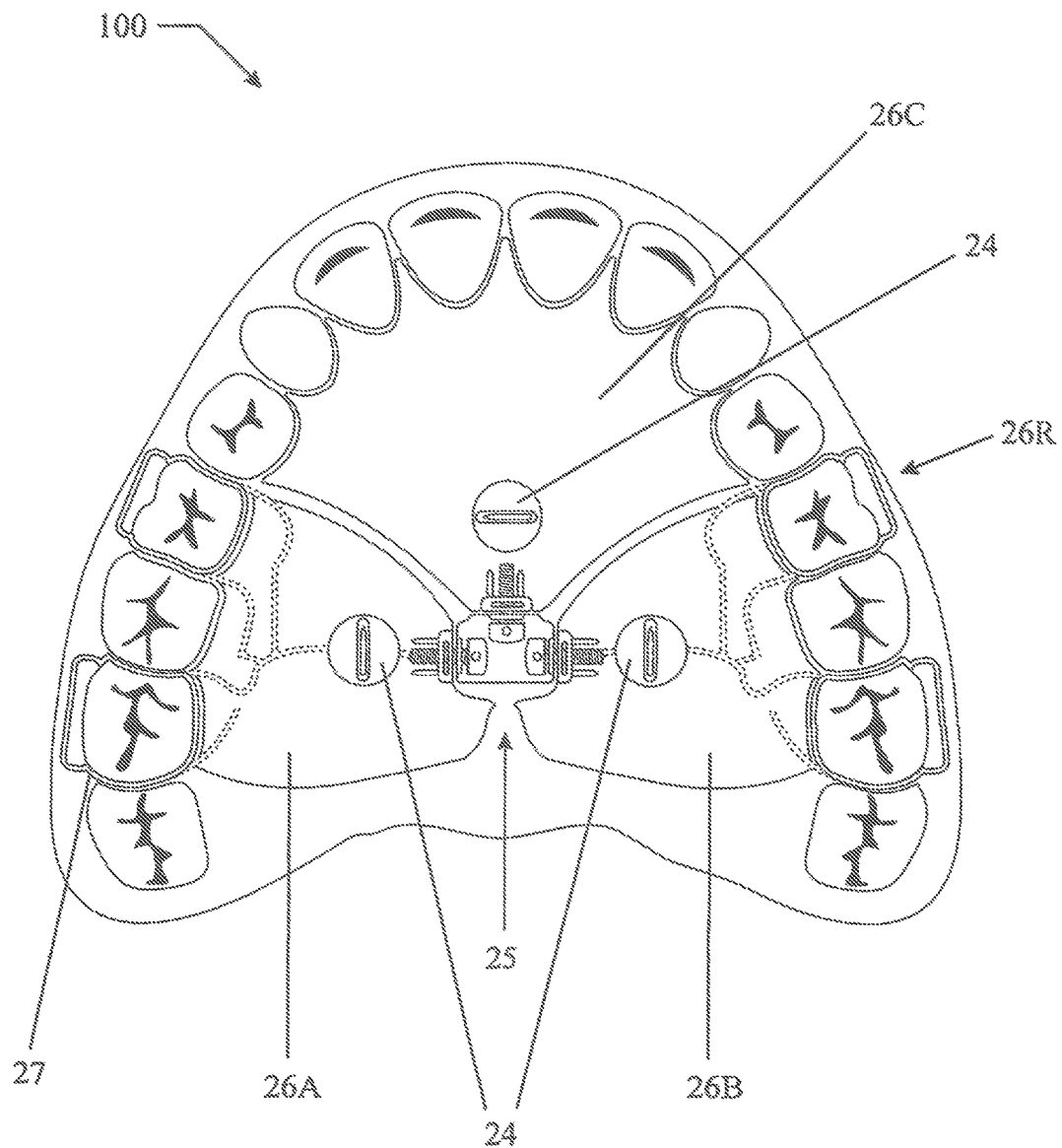
Figure 8C:
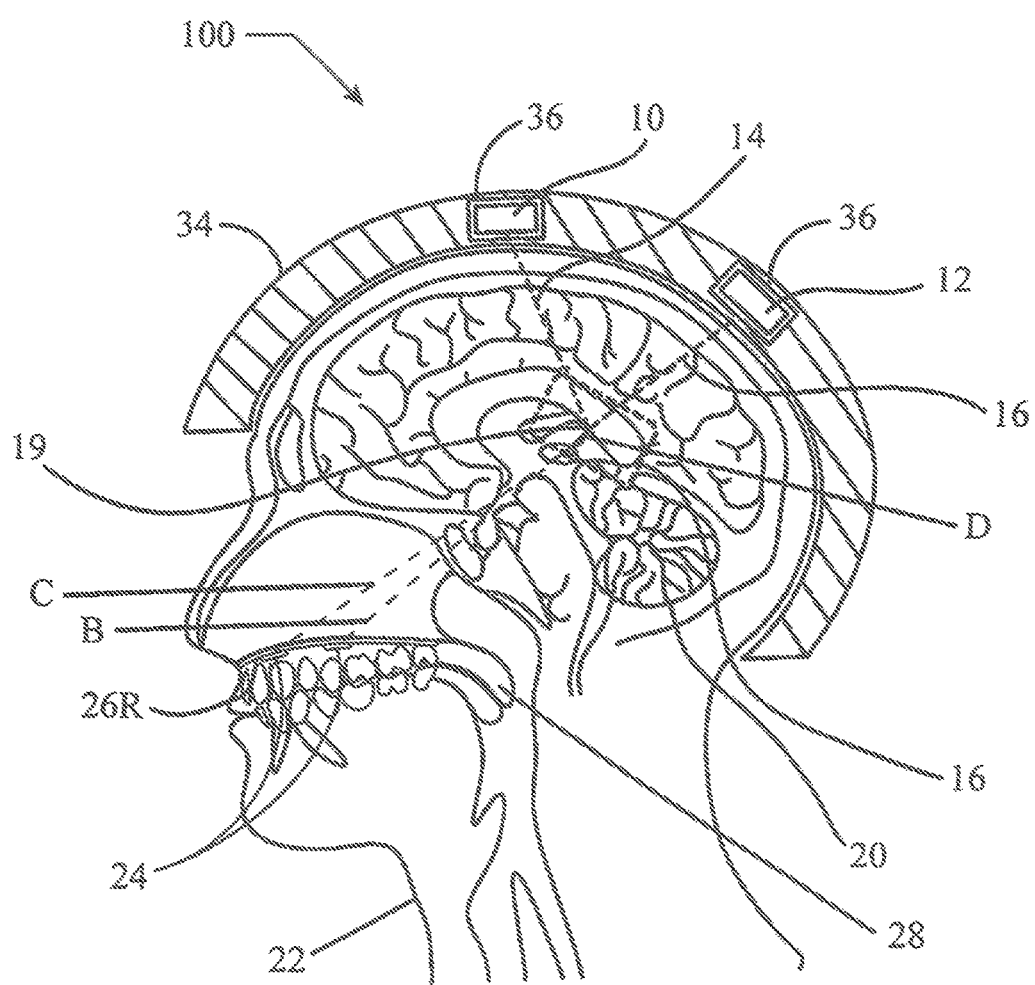
FIG. 8C is a side cross-sectional view of the embodiment of FIG. 8B showing a mouth-roof retaining device located on the roof surface in the mouth of the patient, with the transponders located above the upper teeth of the patient.

In one embodiment, a system for a non-invasive, focused stimulation of in vivo tissue cells is provided, wherein reference points may be established non-invasively with one or more transponders (three transponders in non-limiting embodiments shown in FIGS. 8A, 8B, 8C, 9 and 11). The transponders may be placed in a location so as to provide a reference point relative to the target tissue. In a non-limiting example, the transponders may be placed in a patient's mouth wherein the target tissue for the focused stimulation of tissue includes brain tissue. In a further non-limiting example, the one or more transponders may be associated with an upper surface of the patient's mouth (i.e., the roof of the mouth), as shown in FIGS. 8B and 8C. Referring to FIGS. 8B and 8C, the retaining device 26R can include three pallets 26A, 26B and 26C attached to one another by a central component 25 that is attached to the pallets 26A, 26B, 26C by screws. Wires 27 extend from the screws to attach about upper teeth of the mouth. The mouth-roof retaining device 26R is located on the roof of the mouth with the transponders 24 both spaced above the upper teeth in the mouth.

The transponder(s) may be associated with a retaining device, in a non-limiting embodiment, which may be affixed to the mouth of the patient. The transponder(s) may provide a reference position or plane relative to the target location(s) in the tissue of interest for stimulation. The transponder(s) may be used to track real-time motion of a stimulus of electromagnetic radiation, and detect and provide feedback based on the location of the electromagnetic radiation stimulus/stimuli. The feedback provided by the transponder(s) can be used to ensure the stimuli are directed at the intended target location, and to adjust positioning of the stimuli if necessary. The transponders may be used to focus the stimulus/stimuli at the target tissue area. In another non-limiting embodiment, the transponders may be provided on an upper cranial region of the patient and the electromagnetic radiation/stimuli may be directed upward toward the patient's brain tissue, for example, through the roof of the mouth of the patient.

The target tissue may include a virtual point or virtual points (i.e., in a portion of the target tissue that can be identified with magnetic resonance imaging (MRI) or CAT scan technology, for example). In an embodiment, the system may include a device which may provide multiple energizing stimuli of energy that can be directed to and/or focused on the virtual point(s) in the target tissue. The targeted intersection of the energizing stimuli can be adjusted using the transponder(s) as a reference of the location of the stimuli, in one non-limiting example.

The device may be non-invasively associated with an external portion of a body of a patient, in a non-limiting example. In a further non-limiting example, the device may be fitted to the outer surface of a head of a patient wherein the target tissue is a brain tissue. In another non-limiting example, the device may be placed remote from the patient in a location in which the stimuli being provided there from are targeted at the target tissue of the patient, such that a culmination of the multiple energy stimuli intersect at the target tissue providing sufficient intensity to stimulate the cells of the target tissue. The transponder(s) may be used to detect information about and/or provide feedback to a user of the system regarding a target location and movements of an energizing stimulus. This may occur by way of radiofrequency waves, in one non limiting embodiment.

In further embodiments, digital representations of the virtual target in the target tissue of the patient can be provided to visualize the location of the target during use of the energy stimuli and manipulation thereof, providing another non-limiting non-invasive process for stimulating target neural cells in a patient. In a further embodiment, the system and method herein may include a robot assisted image for guiding the energy stimuli to the targeted location in the target tissue of the patient. In one specific, non-limiting embodiment, the robot may be provided external to the patient, wherein no contact between the robot and the patient is required. In yet a further embodiment, an imaging technology such as CT or MRI may be used to visualize and predefine target locations in the target tissue of a patient. These predefined target locations may be registered with the robot, and the robot may use these predefined target locations to identify and/or provide a visual image for a user of the target locations in a patient tissue to assist in focusing the energy stimuli at the target location.

Turning to the Figures, FIG. 1 is a view of a prior art method of deep brain stimulation which requires electrodes to be surgically implanted at a location in a tissue of a patient to be stimulated. This procedure carries with it risks typically associated with other surgical procedures, and is an invasive procedure.

Figure 2:
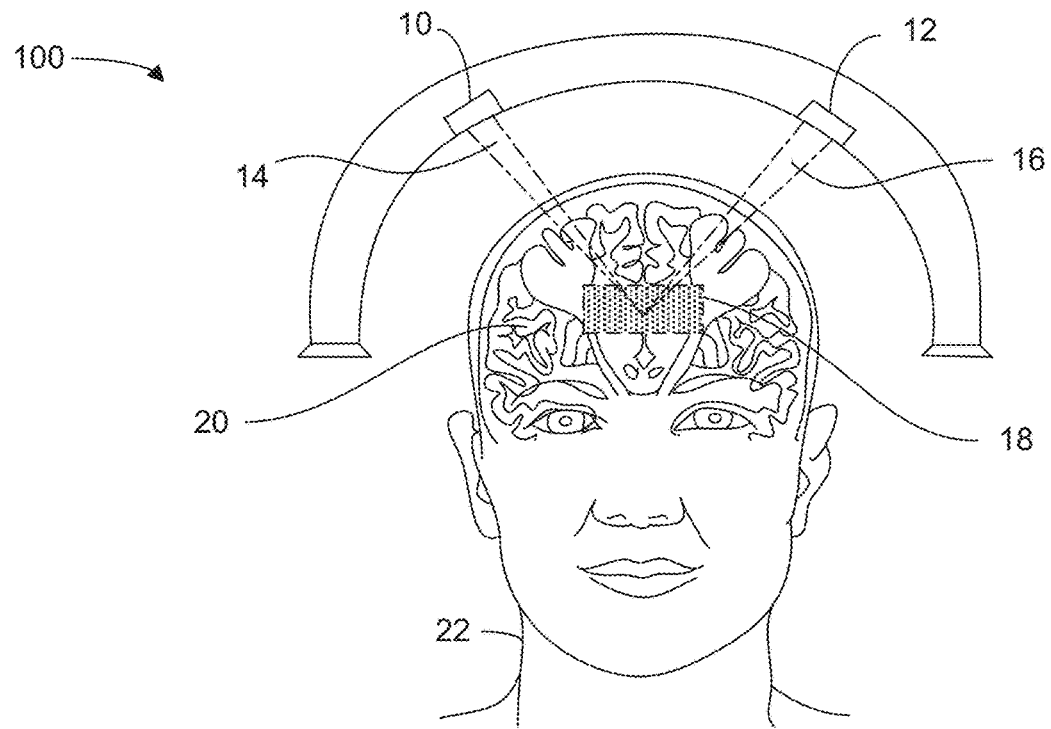
FIG. 2 is a plan view of an embodiment of a system for non invasive in vivo stimulation of nerve cells.

FIG. 2 is a plan view of an embodiment of a system 100 for non invasive in vivo stimulation of nerve cells of a patient as disclosed herein. The system 100 includes a first energy emitting component 10 positioned external to a patient configured to generate a first energy stimulus 14, and a second energy emitting component 12 positioned external to the patient configured to generate a second energy stimulus 16, the first and second energy stimuli are positioned to intersect at a target location 18 in a tissue 20 of the patient 22 having neurons to be stimulated. The first energy stimulus 14 having an intensity level below a predetermined threshold required to stimulate the neurons, and the second energy stimulus 16 has an intensity level below a predetermined threshold required to stimulate the neurons, but a combination of the first and second energy stimuli at the target location 18 in the target tissue 20 of the patient 22 has an intensity level at or above a predetermined threshold required to stimulate the neurons in the target tissue 20 at the target location 18 and prevent the stimulation of neurons outside the target location 18. Each individual energy stimulus may have an intensity level below the predetermined threshold required to stimulate the neurons as described herein in a non-limiting embodiment, such that any tissue encountered by the energy stimulus prior to reaching the target tissue location would not be affected by the stimuli, i.e., would not be stimulated.

In a further embodiment, the first energy emitting component 10 and/or the second energy emitting component 12 may not be in contact with the patient 22 as shown in FIG. 2. In a further non limiting embodiment, the target tissue 20 comprises a brain tissue, and the first and second energy stimuli 14, 16 may be of a sufficient intensity to contact the brain tissue.

In a further embodiment, the first and second energy emitting components 10, 12 are located outside a cranial portion of a patient are positioned such that the first and second energy stimuli are directed through the cranium of the patient toward the target location 18 in a brain tissue to stimulate neurons in the brain tissue. In still a further embodiment, the first and second energy emitting components 10, 12 are located in an intraoral region 28 (shown in FIGS. 8B, 8C and 9) of the patient and a positioned such that the first and second energy stimuli 14, 16 are directed through a roof of the intraoral cavity of the patient toward the target location 18 in a brain tissue to stimulate neurons in the brain tissue.

In still a further embodiment, the system 100 comprises one or more transponder components 24 shown in FIG. 8B and 8C, said transponder components 24 configured to detect a location of the first and/or second energy stimulus 14, 16 and provide a feedback on the location of the first and/or second energy stimulus 14, 16 to a user.

Figure 3:
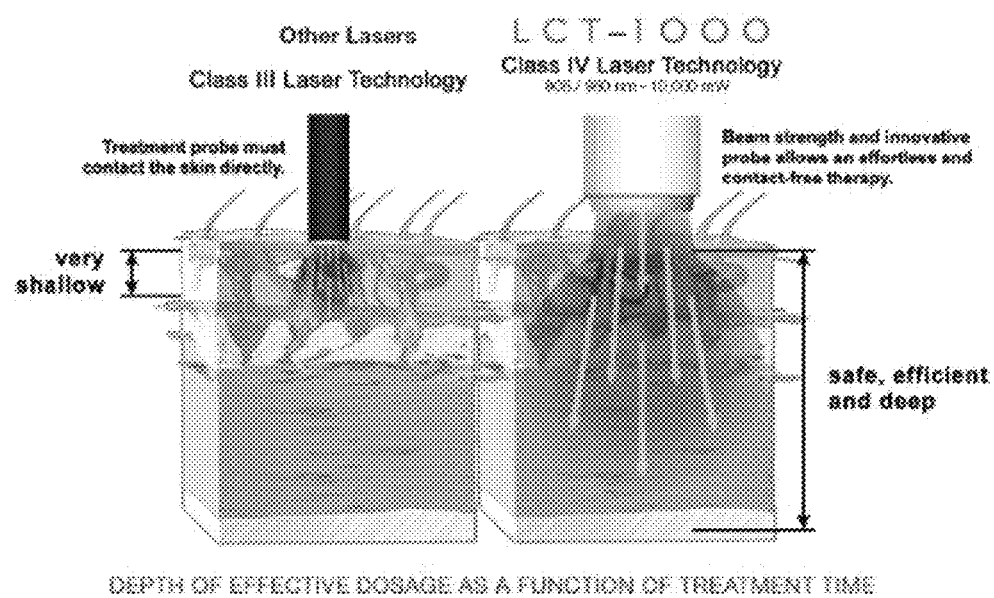
FIG. 3 is a pictorial representation of embodiments of variations of laser technologies and penetration levels.

FIG. 3 is a schematic representation of examples of laser technologies and penetration levels. A class III laser requires the treatment probe to directly contact the skin, and provides relatively shallow penetration of the stimulus, and a class IV laser provides a safe, more efficient and deep penetration of the stimulus with increased stimulus strength and wherein no contact with the skin is necessary. In one non-limiting embodiment of the system described herein, a class IV laser may be used to stimulate the neurons of a patient. In other embodiments of the system, a class III laser may be used for stimulating nerve cells of a patient.

FIGS. 4A-C are schematic and graphical illustrations showing an example of a voltage gradient of a neural cell at rest with a closed pore preventing movement of ions across the neural membrane, wherein the resting neural membrane voltage gradient is −70 mV.

FIGS. 5A-C are schematic and graphical illustrations showing the effect of heat on the neural membrane causing the pore(s) to open allowing the movement of ions across the membrane allowing an ion influx, lowering the voltage gradient of the membrane to −60 mV and increasing the action potential of the neuron. Heating of the neuron has been shown to thicken the membrane to achieve these results. This figure provides one example of how applying low level energy from multiple origins can cause excitation of neurons in the target location at the convergence of the low level energy transmission.

FIGS. 6A-C include graphical and schematic illustrations from Duke et al., showing the transient and selective inhibition of neural activity with infrared light and electrical stimulation and pertain to information disclosed in Duke et al.

FIGS. 7A-B include schematic and graphical illustrations of the effects of heating (stimulating) a neuron during firing of the neuron, resulting in a decrease in the voltage gradient, a depletion of available ions and a decrease in the influx of ions as well as a suppression of the action potential of the neuron.

FIGS. 8A and 8B-8C provide embodiments of the one or more transponder components 24 that may be associated with a retaining device 26 in non-limiting embodiments. The retaining device 26R may be configured to associate with an upper portion of an intra oral region 28 of the patient as shown in FIG. 8B. The three transponders 24 in FIG. 8B are shown as only two transponders in FIG. 8C since it is a side view. The stimulation of brain tissue and feedback from the transponders 24 function similar to the embodiment described below in reference to FIG. 9.

Figure 9:
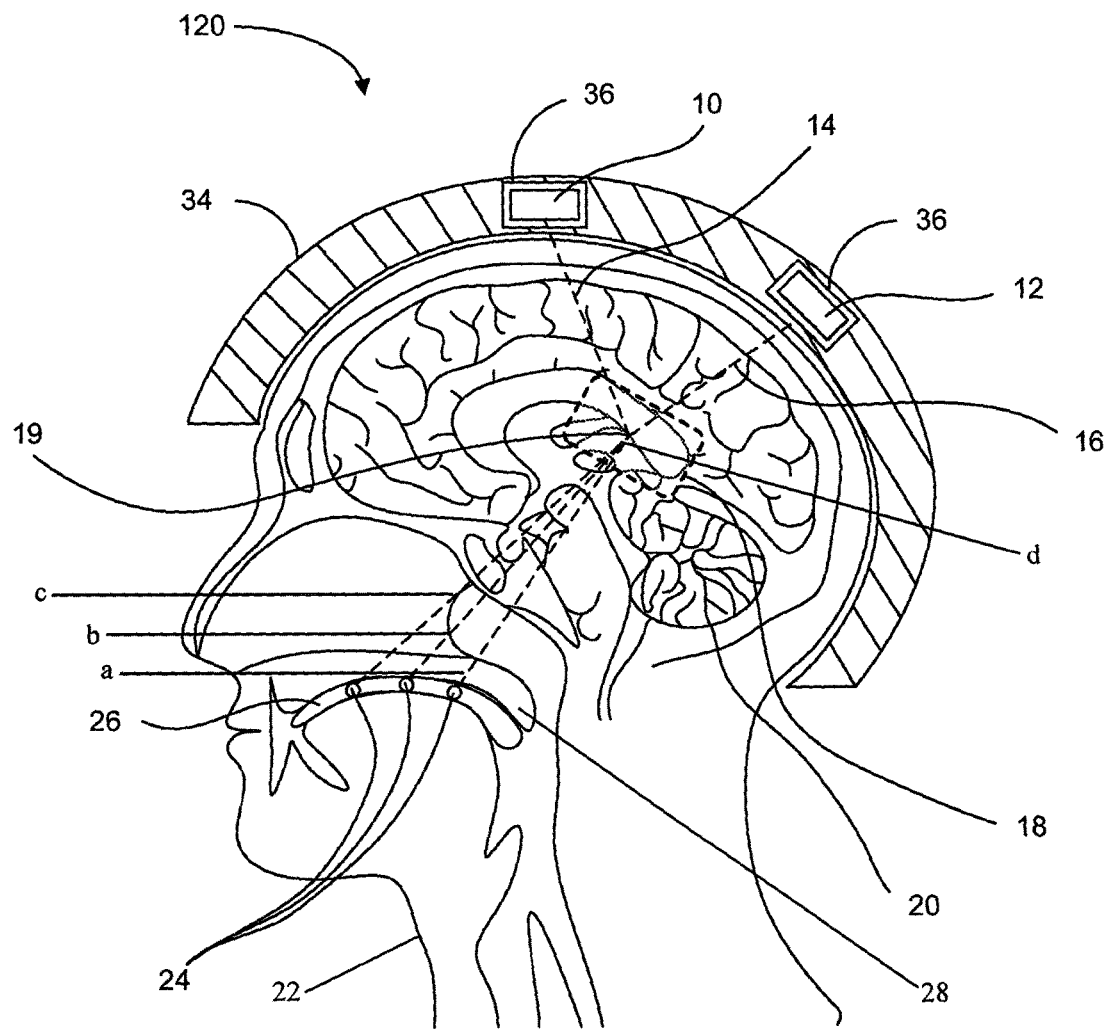
FIG. 9 is a cross sectional view of an embodiment of the system including a headpiece component.

In still a further embodiment, the one or more transponder components may be associated with an outer surface of a head of the patient in a position across from the target location relative to the first and second energy stimuli as shown in FIG. 9. The one or more transponder components 24 are configured to detect a location of the first and/or second energy stimulus 14, 16 and may provide feedback to a user based on the detected location, in a non-limiting embodiment.

FIG. 9 illustrates a system 120 that provides precise, non-invasive, focused stimulation in vivo of brain tissue cells wherein the reference points are established non-invasively with three transponders 24. There are three transponders 24 located in a retainer device 26 placed in an upper portion of an intra oral region 28 of the mouth of a patient 22 in a position across from the target location 18 relative to the first and second energy emitting components 10, 12. The three transponders 24 provide feedback about a location of the first and second energy stimuli 14, 16 relative to the target location 18. Transponder location feedback by way of radio frequency waves, provides three reference points a, b, c, relative to the target tissue 18. The radio frequency waves from transponder reference points a, b, c, intersect at point d within a target point 19 in the target location 18 of target tissue 20.

Further, in the embodiment 120 of the system of FIG. 9, a headwear piece 34 includes one or more rigid secure members 36 which hold the first and second energy emitters 10, 12. The headwear piece 34 may be contoured to direct proper placement onto the patient's head. A non-limiting list of examples of a headwear piece useful in accord with the teachings herein include, but are not limited to, elastic bands, hat, helmet, or toupee, or a combination thereof.

In still a further embodiment, the first and second energy emitting components 10, 12 direct the first and second energy stimuli 14, 16 from a position external to the patient toward a cranial cavity to a target location 18 in a brain tissue of the patient 22, and the one or more transponder components 24 are provided in an intraoral region 28 of the patient 22, in a non-limiting embodiment. The one or more transponder components 24 are configured to provide a feedback of the location of the first and/or second energy stimuli 14, 16, and/or feedback of the location of the first and/or second energy stimuli 14, 16, relative to the target location 18. In other non-limiting embodiments, the transponder units may be located external to the intraoral region of the patient, for example, the transponder unit(s) may be provided under a mandibular portion of the patient or near the neck region.

Figure 10:
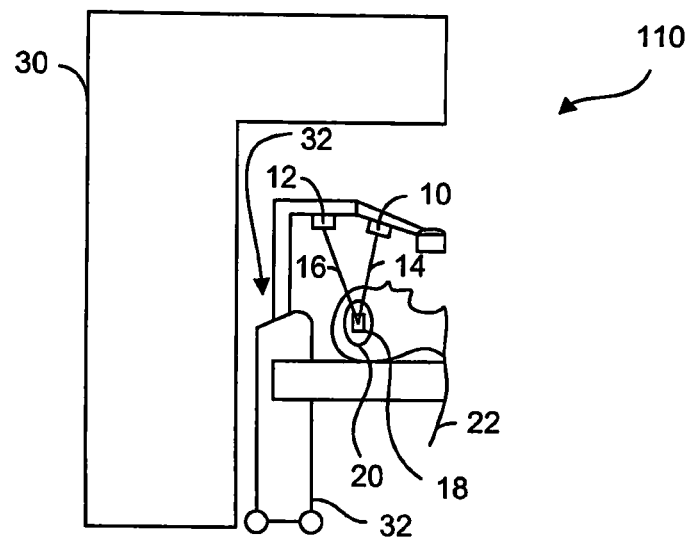
FIG. 10 is a schematic of an embodiment of a system for stimulating neurons of a patient in vivo comprising an imaging system component and a robotic component.

In a further embodiment shown in FIG. 10, a system for stimulating neurons of a patient in vivo 110 may be provided. The system embodiment 110 may include an imaging system component 30, such as a CT imaging machine or MRI machine in non-limiting embodiments. The imaging system component 30 may be configured to provide visualization of a tissue 20 of the patient such that the target location 18 in the tissue 20 can be identified. This visualization may occur before a procedure in which the neurons are to be stimulated in vivo, during the stimulation procedure, or following the stimulation procedure. The imaging system component may provide a visualization of the target tissue 20 which can be used to guide the first and second energy emitting components 10, 12, to direct the first and second energy stimuli 14, 16 at the target location 18. If performed before or after the stimulation procedure, CT or MRI images may be taken of the patient and the target location 18 to enable a user to view the target prior to or following the scan. If visualization occurs during the stimulation procedure, images may also be taken via MRI or CT scan.

FIG. 10 further shows a robotic component 32, which can receive and transmit information regarding the target location 18 and/or the target tissue 20 in the patient 22, as well as other information regarding the system 100, 110. The target location 18 information obtained from the imaging system component 30 may be provided to the robotic component 32 for use during the procedure or during a subsequent procedure, in one non-limiting embodiment. The robotic component 32 may provide information about the target location 18 and feedback to a user about the location of the first and/or second energy stimulus 14, 16 relative to the target location 18. The robotic component 32 can alternatively be removably, non-invasively coupled to the patient near the target tissue 20, and the energy emitting components 10, 12 may be associated with the robotic component 32 in a non-limiting embodiment. The robotic component 32 may be used in conjunction with the transponder components 24 to accurately target the intersection of the energy stimuli 14, 16 at the target location 18 and to adjust the location of the energy stimuli 14, 16 relative to the target location 18 as necessary for effective stimulation of the neural cells at the target location 18, in a non-limiting embodiment. The robotic component 32, in conjunction with the transponder components 24, will also allow for adjustments of the location of the projected energy stimuli 14, 16, due to, for example, movement of the patient during a procedure. This embodiment will provide a non-invasive robot-assisted guiding option for targeting the target location 18 of the patient.

Figure 11:
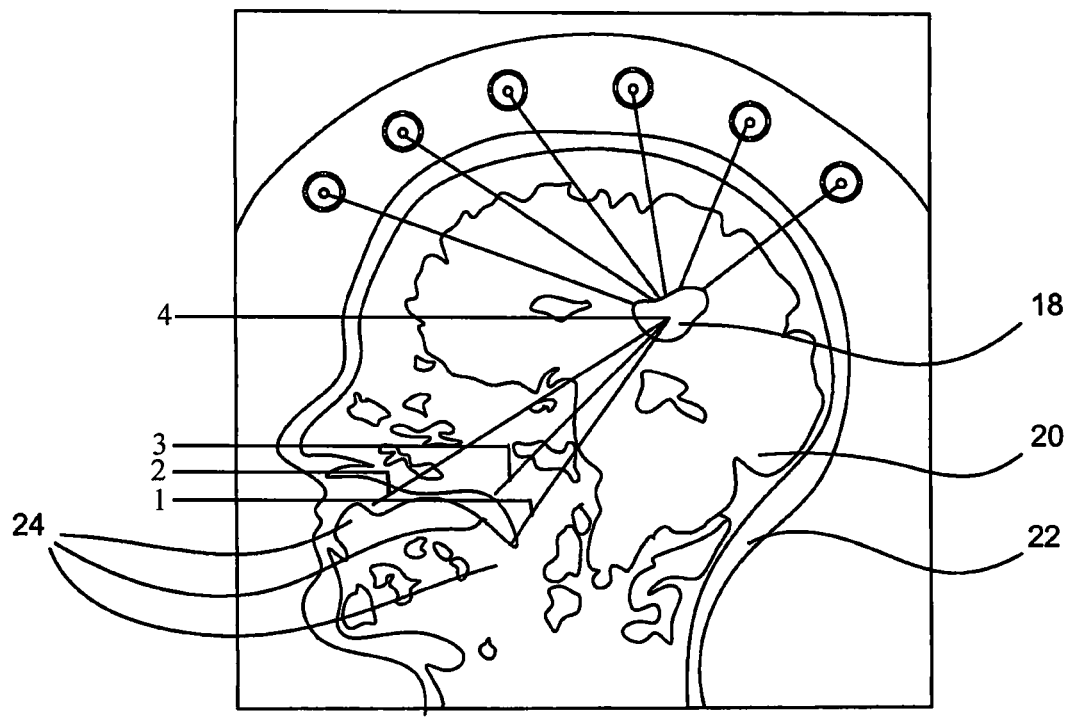
FIG. 11 is a cross sectional schematic view of another embodiment of a system for stimulating neurons of a patient in vivo comprising transponder components.

FIG. 11 is a cross sectional schematic view showing a scan image of a patient's cranial cavity and demonstrating the use of a non-limiting embodiment 110 of the system for stimulating neurons of a patient in vivo. The embodiment includes transponder components 24 which detect and provide location information regarding the energy stimuli 14, 16. This information can be used to adjust a position of the energy emitting components 10, 12 relative to the target tissue 20 and target location 18 as necessary. The three transponder components 24 provide reference points 1, 2, 3 and are disposed in the intraoral cavity of the patient 22 as shown in FIG. 11. The radio frequency waves from transponder reference points 1, 2, 3, intersect at target point 4 within the target location 18 shown as illuminated by the energy stimuli 14, 16. A scan image similar to that shown in FIG. 11 may be produced by the image system component 30 to provide visualization of the components of the system and the target location 18 relative to the energy stimuli 14, 16, for example to a user of the system 110 in non-limiting embodiments to assist in tuning and focusing the energy to the target location 18.

Figure 12:
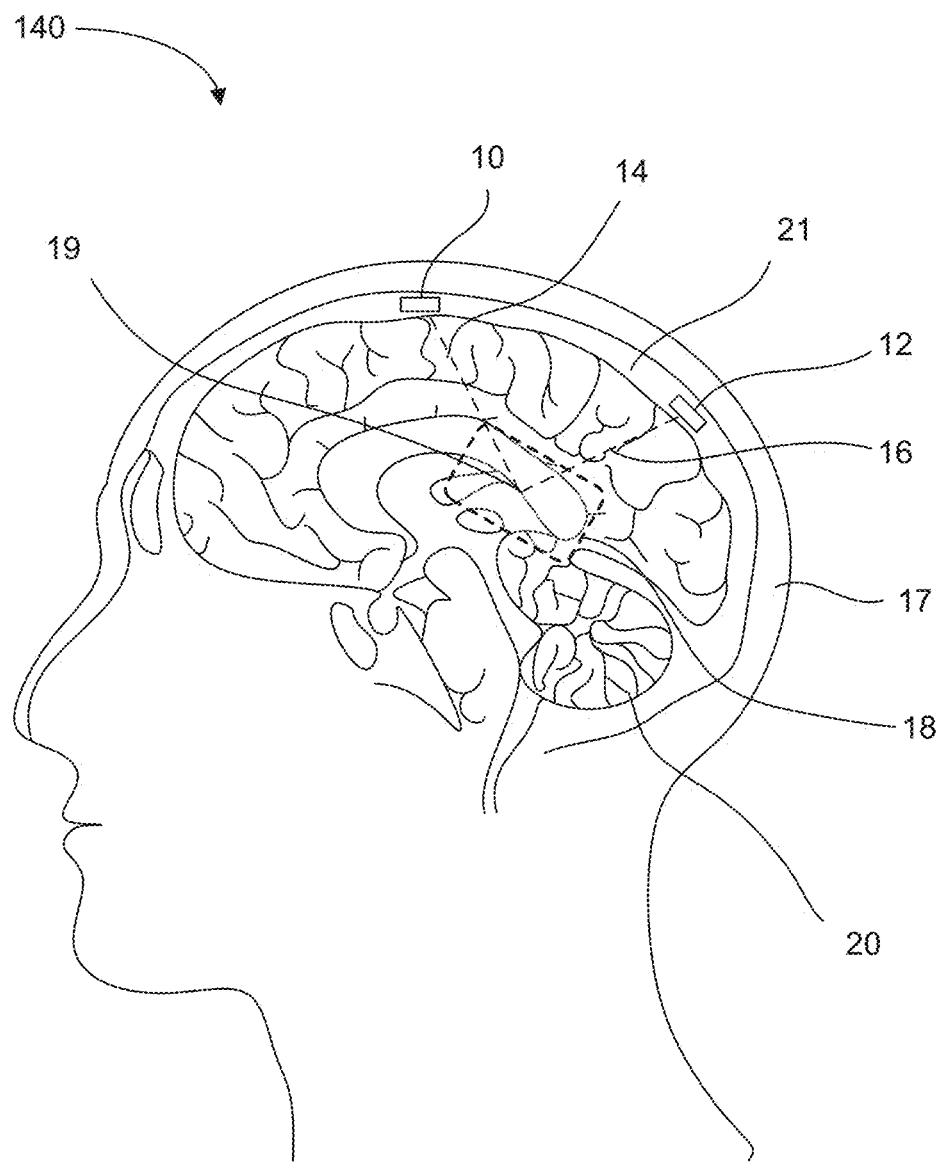
FIG. 12 is a cross sectional view of an alternative embodiment of a system for stimulating neurons in a patient in vivo wherein the energy emitting components are positioned between the cranium and a brain tissue of the patient.

In still a further embodiment, shown in the cross sectional view of FIG. 12, a system 140 for stimulating neurons in a target tissue 18 of a patient in vivo may be provided wherein the first and/or second energy emitting components 10, 12, may be positioned between a cranium 17 and a brain tissue 20 of the patient, in the dura mater, for example, or in the subdural space 21 of the patient, for example, wherein the target tissue is the brain tissue 20 in which the neurons to be stimulated are located, in a non-limiting embodiment. Insertion of the energy emitters 10, 12 beneath the cranium 17 and positioning of the energy emitters 10, 12 in the subdural space 21 may provide a safer and less traumatic option than the more invasive procedure of inserting probes into the brain tissue 20.

The energy emitters 10, 12 described in non-limiting embodiments herein may include dynamic directional capabilities, allowing them to be precisely positioned and directed at the target location 18. Adjustability of the energy emitters 10, 12 may occur from outside the body of the patient before, during, or after the insertion of the energy emitters 10, 12 under the cranium 17 of the patient, in the non-limiting embodiment in which the energy emitters 10, 12 are positioned within the body of the patient. Adjustability of the energy emitters 10, 12 as described herein may also be beneficial for the embodiments in which the energy emitters 10, 12, are placed external to the patient. The dynamic directional feature of the energy emitters 10, 12, provides an advantage wherein the energy stimuli 14, 16 emitted there from can be focused on the target location 18 in the target tissue 20. Consequently, the energy stimuli 14, 16 may be directed to intersect at a target point 19, as shown in FIG. 12, to stimulate the neurons at the target location 18. As described herein, in a non-limiting embodiment, the energy stimuli 14, 16 provided from the first and second energy emitters 10, 12, may be of an intensity below a threshold required to stimulate the neurons at the target location 18, however, the combined stimuli 14, 16, at the target point 19 may reach an intensity at or above a required threshold level required to stimulate the neurons at the target point 19 in the target region 18 of the target tissue 20. As aforementioned, the individual stimuli 14, 16 provided at a level below the intensity threshold at which the neurons can be stimulated provides the ability to direct the energy stimuli 14, 16, through a non-target tissue or non-target tissue region(s) before reaching the target location 18 without causing damage to the non-target tissue or non target tissue region(s) through which the energy stimuli 14, 16 pass before intersecting with one another.

As shown in the embodiment provided in FIG. 12, the system 140 may include a first energy emitting component 10 positioned under the cranium 17 of the patient, said first energy emitting component 10 positioned under the cranium 17 configured to generate a first energy stimulus 14, and a second energy emitting component 12 positioned under the cranium 17 of the patient configured to generate a second energy stimulus 16, the first and second energy stimuli 14, 16, are positioned to intersect at a target location 18 in a tissue 20 of the patient having neurons to be stimulated. In a non-limiting embodiment, the first energy stimulus 14 may have an intensity level below a predetermined threshold required to stimulate the neurons, and the second energy stimulus 16 may have an intensity level below a predetermined threshold required to stimulate the neurons, but a combination of the first and second energy stimuli 14, 16 at an intersection of the first and second energy stimuli 14, 16 at a target point 19 in the target location 18 of the target tissue 20 of the patient may have an intensity level at or above a predetermined threshold required to stimulate the neurons in the target tissue 20 at the target location 18, in order to prevent the stimulation of neurons and/or the damage of tissue outside the target location 18.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed. It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A non-invasive system for stimulating neurons of a patient in vivo, comprising:
    a first ultrasound energy emitter positioned external to a patient configured to generate a first ultrasound energy stimulus at a first intensity level below a first predetermined threshold required to stimulate the neurons of the patient;
    a second ultrasound energy emitter positioned external to the patient configured to generate a second ultrasound energy stimulus at a second intensity level below a second predetermined threshold required to stimulate the neurons of the patient wherein the first ultrasound energy stimulus and second ultrasound energy stimulus are positioned to intersect at a target location in a target tissue;
    an imaging system configured to visualize a tissue of the patient such that the target location is identified;
    a mouth-roof retaining device adapted to be located on a roof surface in a mouth of the patient, the mouth-roof retaining device comprising a first pallet, a second pallet and a third pallet, each pallet being separate from one another, a central component for attaching inner ends of each of the pallets together by screw fasteners, wires extending from at least two of the screw fasteners adapted for attaching the central component to teeth in the mouth of the patient;
    a plurality of transponders comprising a first transponder on the first pallet, a second transponder on the second pallet and a third transponder on the third pallet; and
    the first transponder and the second transponder and the third transponder are positioned opposite the target location relative to the first and the second ultrasound energy emitters to provide a reference position to the target location, the first transponder and the second transponder and the third transponder provide feedback and ensure the first ultrasound energy stimulus and the second ultrasound energy stimulus are directed at the target location and to adjust positioning of the first ultrasound energy stimulus and/or the second ultrasound energy stimulus, wherein the first transponder and the second transponder and the third transponder are adapted to be located on the mouth-roof retaining device and are above exposed surfaces of the teeth in the mouth of the patient, and wherein said first and said second ultrasound energy emitters are secured to a headwear piece.

2. The system of claim 1, wherein the first ultrasound energy emitter and the second ultrasound energy emitter are in a support that located above and is not in direct contact with the patient.

3. The system of claim 1, wherein the target tissue comprises a brain tissue, and wherein the first and second ultrasound energy stimuli each comprise an intensity to contact the brain tissue.

4. The system of claim 1, wherein the first and the second ultrasound energy emitters are disposed outside a cranial portion of the patient and are positioned such that the first and second ultrasound energy stimuli are directed through the cranium of the patient toward the target location in a brain tissue to stimulate neurons in the brain tissue.

5. The system of claim 1, wherein the first and second ultrasound energy emitters direct the first and second ultrasound energy stimuli from a position external to the patient toward a cranial cavity to the target location in a brain tissue of the patient.

6. A non-invasive method of stimulating neurons in vivo, the method comprising steps of:
    generating a first ultrasound energy stimulus and a second ultrasound energy stimulus;
    directing the first and second ultrasound energy stimuli at a target location in a tissue of a patient comprising neurons to be stimulated, wherein an intensity of the first ultrasound energy stimulus and the second ultrasound energy stimulus are each below a predetermined threshold level required to independently stimulate one or more neurons in a target tissue, and wherein combination of the first and second ultrasound energy stimuli at the target location comprises an intensity at or above the predetermined threshold level to stimulate one or more neurons at the target location and prevent the stimulation of neurons outside the target location;

providing an imaging system configured to visualize a tissue of the patient such that the target location is identified;

providing a mouth-roof retaining device located on a roof surface in a mouth of the patient, the mouth-roof retaining device comprising a first pallet, a second pallet and a third pallet, each pallet being separate from one another, a central component for attaching inner ends of each of the pallets together by screw fasteners, wires extending from at least two of the screw fasteners adapted for attaching the central component to teeth in the mouth of the patient;

providing three transponders with three reference points, the three transponders comprising a first transponder on the first pallet, a second transponder on the second pallet and a third transponder on the third pallet, the three transponders in the mouth-roof retaining device located on a roof surface in the mouth of the patient, with the three transponders located above exposed surfaces of the teeth in the mouth of the patient;

providing the three transponders with the three reference points be in a position opposite the target location relative to first and second ultrasound energy transmitters;

focusing the three reference points of the three transponders on the target location in the target tissue;

providing feedback from the three transponders to a user to ensure the first ultrasound energy stimulus and the second ultrasound energy stimulus are directed at the target location and to adjust positioning of the first ultrasound energy stimulus and/or the second ultrasound energy stimulus;

stimulating the neurons, with the first ultrasound energy stimulus and the second ultrasound energy stimulus at the target location and preventing the stimulation of neurons outside the target location; and providing a headwear piece for securing the first and second ultrasound transmitters for generating the first ultrasound energy stimulus and the second ultrasound energy stimulus, or providing a robot which provides at least one of information about the target location, information about re-targeting, and feedback to a user about the location of the first and/or second ultrasound energy stimulus relative to the target location.

7. The method of claim 6, wherein the first ultrasound energy stimulus and second ultrasound energy stimulus are emitted at the target location in the tissue of the patient from a support located in a location external to and not in direct contact with the patient.

8. A system for stimulating neurons in a brain tissue of a patient in vivo, comprising:

a first ultrasound energy emitter configured to be disposed around the head of a patient projecting inwards towards the brain tissue, said first ultrasound energy emitter being configured to generate a first ultrasound energy stimulus, and a second ultrasound energy emitter configured to be disposed around a head of a patient projecting inwards towards the brain tissue, said second ultrasound energy emitter being configured to generate a second ultrasound energy stimulus, wherein the first and second ultrasound energy stimuli are positioned to intersect at a target location in the brain tissue of the patient comprising neurons to be stimulated; wherein the first ultrasound energy stimulus comprises an intensity level below a predetermined threshold required to stimulate the neurons, and the second or more ultrasound energy stimulus comprises an intensity level below a predetermined threshold required to stimulate the neurons; and wherein a combination of the first and second or more ultrasound energy stimuli at the target location in the brain tissue of the patient comprises an intensity level at or above a predetermined threshold required to stimulate the neurons at the target location and prevent the stimulation of neurons outside the target location;

an imaging system configured to visualize a tissue of the patient such that the target location is identified;

a mouth-roof retaining device comprising a first pallet, a second pallet and a third pallet, each pallet being separate from one another, a central component for attaching inner ends of each of the pallets together by screw fasteners, wires extending from at least two of the screw fasteners adapted for attaching the central component to teeth in the mouth of the patient;

a plurality of transponders associated with the mouth-roof retaining device which adapted to be located on a surface of a roof of a mouth of the patient, the plurality of transponders comprising a first transponder on the first pallet, a second transponder on the second pallet and a third transponder on the third pallet;

the plurality of transponders are positioned opposite the target location relative to the first and the second ultrasound energy emitters and configured to provide feedback and information to a user on re-targeting for the location of the first ultrasound energy stimulus and/or the second ultrasound energy stimulus, wherein the plurality of transponders are adapted to be located on the mouth roof retaining device and are above exposed surfaces of the teeth in the mouth of the patient; and a robot, wherein said identified location from the imaging system is provided to the robot and said robot provides at least one of information about the target location, information about re-targeting, and feedback to a user about the location of the first and/or second ultrasound energy stimulus relative to the target location.

* * * * *